(12) United States Patent
Wall

(10) Patent No.: US 6,423,270 B1
(45) Date of Patent: Jul. 23, 2002

(54) FLOW CYTOMETRIC CHARACTERIZATION OF AMYLOID FIBRILS

(75) Inventor: Jonathan Stuart Wall, Knoxville, TN (US)

(73) Assignee: University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/843,751

(22) Filed: Apr. 30, 2001

Related U.S. Application Data

(62) Division of application No. 09/302,963, filed on Apr. 30, 1999, now Pat. No. 6,245,572.
(60) Provisional application No. 60/083,864, filed on May 1, 1998.

(51) Int. Cl.⁷ .................................................. G01N 1/00
(52) U.S. Cl. ......................... 422/61; 436/63; 436/164; 436/172; 435/4; 435/29
(58) Field of Search ........................ 436/63, 164, 171, 436/172, 805, 811, 815; 435/4, 29, 810, 975; 422/61

(56) References Cited

U.S. PATENT DOCUMENTS

| | | | |
|---|---|---|---|
| 4,738,932 A | * 4/1988 | Yabusaki | 436/571 |
| 5,262,332 A | * 11/1993 | Selkoe | 436/518 |
| 5,276,059 A | 1/1994 | Caughey et al. | 514/647 |
| 5,354,654 A | * 10/1994 | Ligler et al. | 435/5 |
| 5,424,221 A | * 6/1995 | Westermark et al. | 436/518 |
| 5,474,893 A | 12/1995 | Fang | 435/4 |
| 5,486,460 A | * 1/1996 | Townsend | 435/40.51 |
| 5,540,494 A | 7/1996 | Purvis, Jr. et al. | 356/73 |
| 5,935,927 A | 8/1999 | Vitek et al. | 514/12 |

OTHER PUBLICATIONS

*Chemical Abstracts*, vol. 120, No. 9, Feb. 28, 1994, Abstract 103899.
C.L. Shen et al., "Light Scattering Analysis of Fibril Growth from the Amino–Terminal Beta(1–28) Fragment of Beta–amyloid Peptide", *Biophysical Journal*, vol. 65, No. 6, pp. 2383–2395 (1993).
*Biological Abstracts*, vol. 84, Abstract No. 110517, 1987.
M. Palutke et al., "Flow Cytometric Purification of Alzheimer's Disease Amyloid Plaque Core Using Thioflavin T.", *Cytometry*, vol. 8, No. 5, pp. 494–499 (1987).

* cited by examiner

*Primary Examiner*—Maureen M. Wallenhorst
(74) *Attorney, Agent, or Firm*—Morgan, Lewis & Bockius LLP

(57) ABSTRACT

A method of detecting amyloid fibrils in biological samples utilizing flow cytometry is described. It has been found that the measurement of fluorescence from amyloidophilic dyes, such as thioflavin T and Congo red, as well as side scatter and forward scatter measurements are particularly useful in detecting the presence of amyloid fibrils. Flow cytometric detection of amyloid fibrils in subjects such as humans and livestock can be employed for diagnosis, assessment of therapeutic efficacy, research, and monitoring of livestock for the presence of infectious amyloidosis.

25 Claims, 7 Drawing Sheets

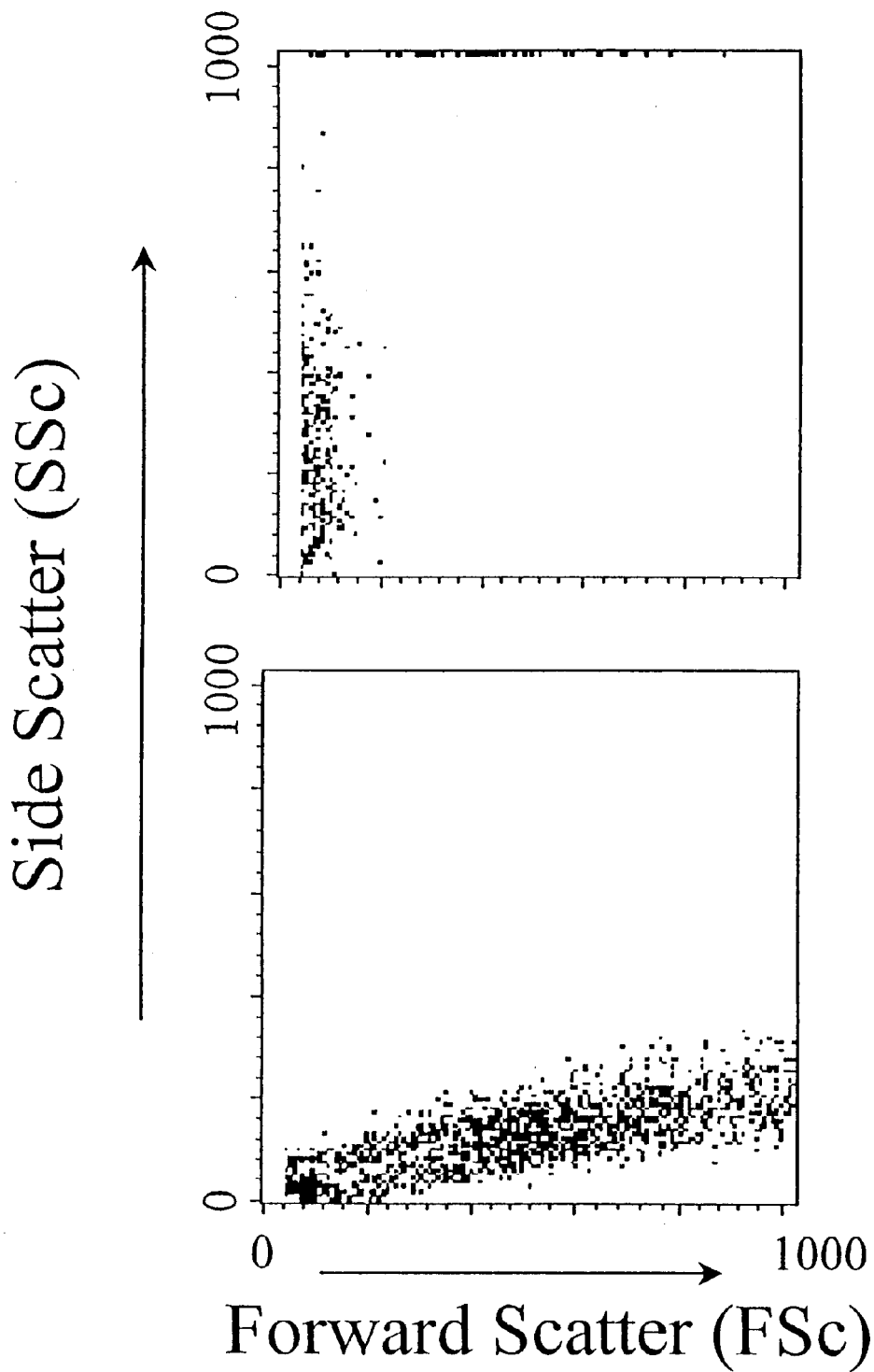

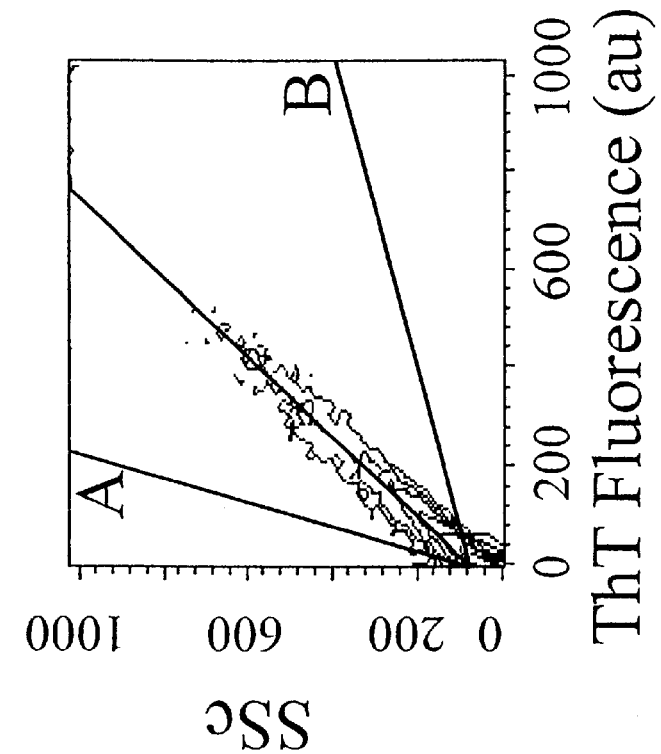
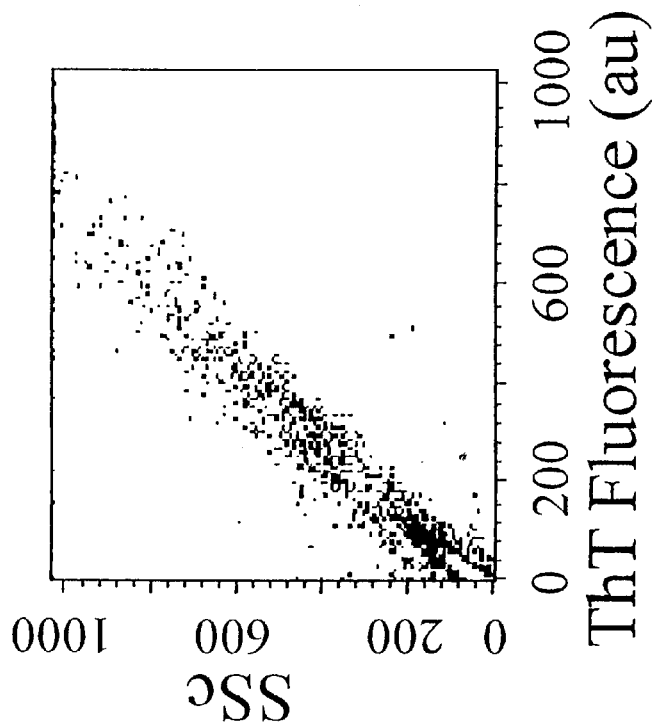

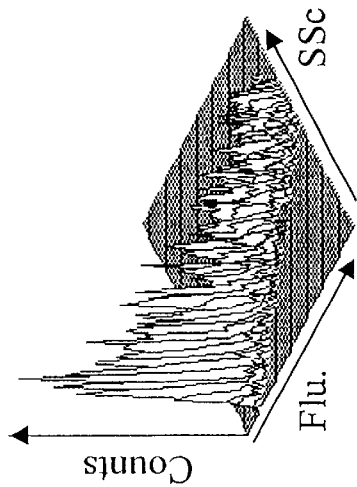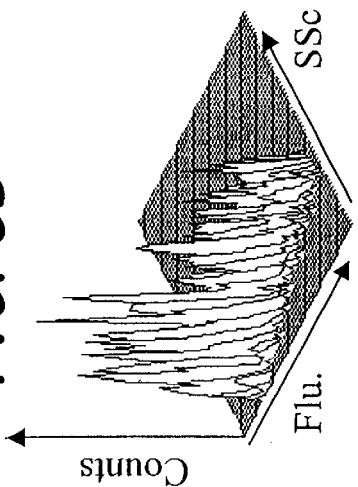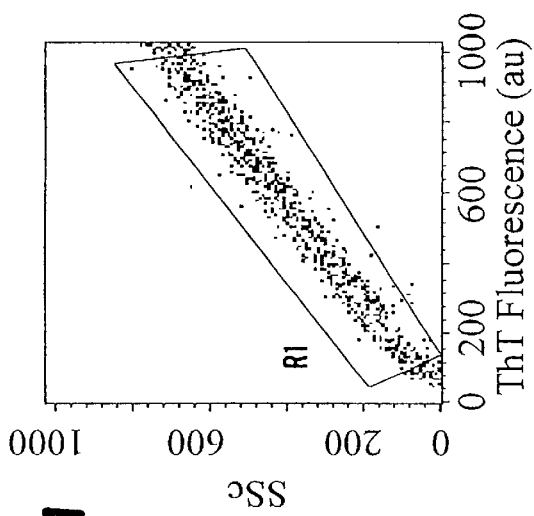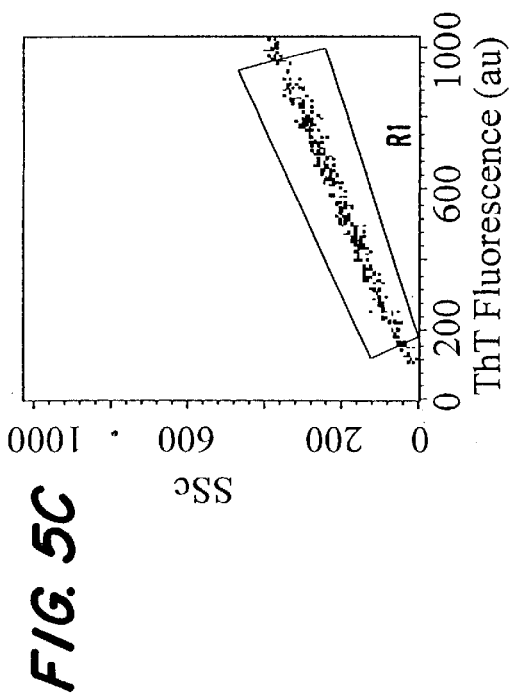

FLOW CYTOMETRIC CHARACTERIZATION OF AMYLOID FIBRILS

CROSS-REFERENCE TO RELATED APPLICATIONS

This application is a divisional of application Ser. No. 09/302,963, filed Apr. 30, 1999, now U.S. Pat. No. 6,245,572 issued on Jun. 12, 2001, which claims the benefit of U.S. provisional application No. 60/083,864, filed May 1, 1998, all of which are incorporated herein by reference in their entirety.

FEDERAL SUPPORT

This invention was made with government support under Grant T35 DK07405-13, awarded by The National Institutes of Health. Thus, the government may have certain rights in this invention.

TECHNICAL FIELD

The present invention relates to flow cytometry methods for detecting the presence of amyloid fibrils in biological samples for diagnostic, research and therapeutic purposes.

BACKGROUND OF THE INVENTION

Amyloid fibrils are aggregates of normally soluble, innocuous proteins whose deposition is associated with a group of diseases known as amyloidoses. Conditions mediated by the presence of amyloid fibrils include Alzheimer's disease, inflammation-associated amyloid type II diabetes, bovine encephalopathy (BSE), Creutzfeld-Jakob disease (CJD), scrapie and primary amyloidosis. Fibrillogenesis or fibril formation has been monitored in vitro using a combination of turbidity, light scattering and fluorescence measurements yielding both equilibrium and kinetic information. For additional material regarding transmissible spongiform encephalopathies, infectious and noninfectious amyloids, subacute spongiforrn encephalopathies, and prisons, refer to B. Chesebro et al., "Transmissible Spongiform Encephalopathies: A Brief Introduction," in *FIELDS VIROLOGY* 2845–2850 (Third ed., B. N. Fields et al., editors; Lippincott-Raven Publ., Philadelphia, Pa. 1996); D. C. Gajdusek, "Infectious Amyloids: Subacute Spongiform Encephalopathies as Transmissible Cerebrai Amyloidoses" in *FIELDS VIROLOGY* 2851–2900; S. B. Prusiner, "Prisons" in *FIELDS VIROLOGY* 2901–2950; L. W. Heck "The Amyloid Diseases" in *CECIL TEXTBOOK OF MEDICINE* 1504–6 (20th edition, J. C. Bennett et al, editors; W. B. Saunders Co., Philadelphia, Pa., 1996), and the references disclosed therein; these references are herein incorporated by reference in their entirety.

SUMMARY OF THE INVENTION

The present invention provides methods for detecting amyloid fibrils by flow cytometric analysis. These methods analyze biological samples, such as blood, urine, peritoneal fluid, fat samples or aspirates, cerebrospinal fluid (CSF), and stool, and provide a means for detecting amyloid fibrils for purposes of assessing treatment and general therapy efficacy, diagnosis, research, and monitoring of livestock for the presence of transmissible amyloidoses.

In one embodiment, the presence of amyloid fibrils in a biological sample is detected by the following general method. The autofluorescence of a biological sample is optionally determined. A first amyloidophilic dye is added to the sample which is then subjected to flow cytometry analysis and data is collected therefrom. Next, a second amyloidophilic dye is added to the sample which is subjected to flow cytometry analysis and data is collected therefrom. From this data the presence of amyloid fibrils in the biological sample is determined.

In another embodiment, the presence of amyloid fibrils in a biological sample is detected by the following method. A first amnyloidophilic dye is added to a biological sample followed by flow cytometry analysis. A second amyloidophilic dye is then added to the sample and flow cytometry analysis is repeated. From the data collected from the flow cytometry analysis, it is determined whether there is a linear dependence between forward scatter and side scatter. The sample is also evaluated to see if it is positive for fluorescence of the first and second amyloidophilic dyes. The positive fluorescence determinations may then be used to calculate an amyloid burden index. Using this index the presence of amyloid fibrils in the biological sample is determined.

BRIEF DESCRIPTION OF THE DRAWINGS

FIGS. 1A–1B: The scattering patterns are compared for (A) amorphous aggregates formed by prolonged sonication of a BJp (CRO) at 1 mg/ml and (B) fibrillar aggregates formed by hydration of Aβ (25–35) at 1 mg/ml.

FIGS. 4A–4B: Panel (A) shows a linear relationship between side scatter (SSc) and ThT fluorescence in linear mode for Aβ (25–35) amyloid fibrils. Panel (B) shows a computer-generated analysis of the data in (A).

FIGS. 5A–5D: Synthetic Aβ (25–35) amyloid fibrils prepared by hydration in PBS then labeled with ThT (panels A and B) showed less binding of ThT than when identical amyloid fibrils were labeled during hydration (panels C and D).

MODES OF CARRYING OUT THE INVENTION

General Description

Figure 2A:
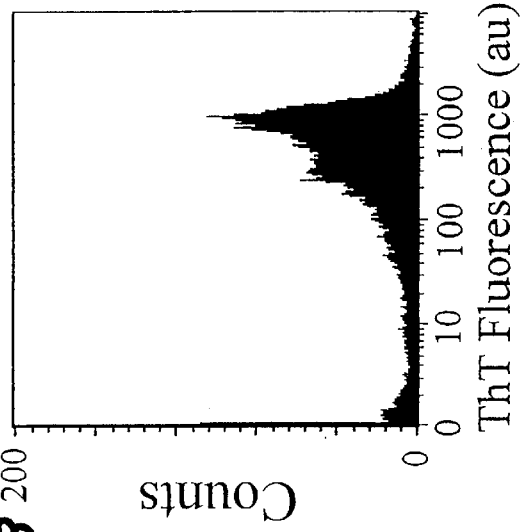
FIGS. 2A–2D: The dual fluorescence labeling of Aβ (25–35) amyloid fibrils with Congo red (CR) and thioflavin T (ThT) is shown. Panel (A) shows scattering patterns of the amyloid fibrils; panel (B) quantifies the amount of ThT fluorescence without CR; panel (C) quantifies the amount of CR fluorescence in the presence of ThT; and panel (D) shows the fluorescence of both CR and ThT.
Figure 2B:
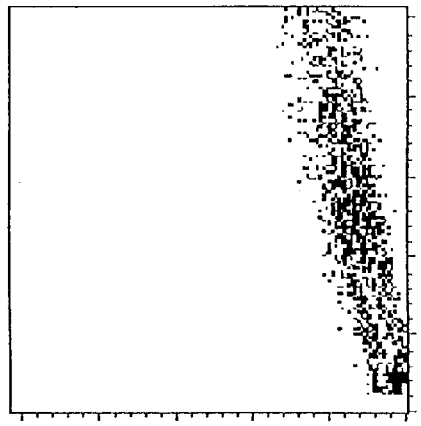
Figure 2C:
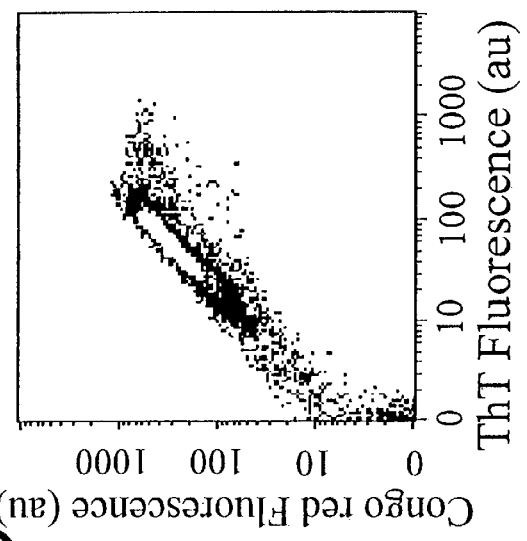
Figure 2D:
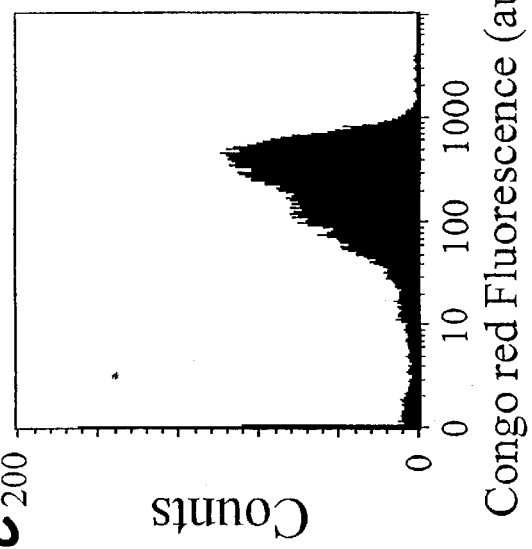
Figure 3A:
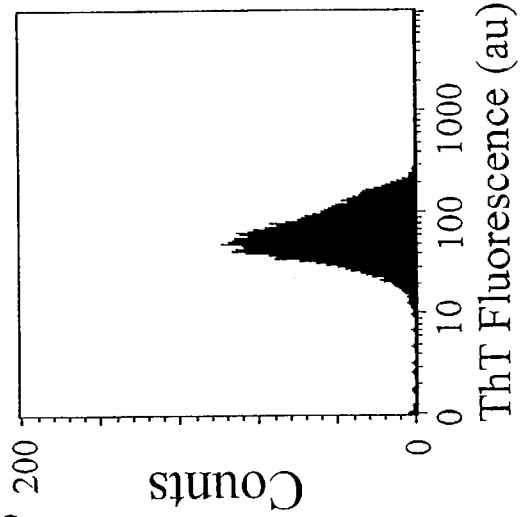
FIGS. 3A–3D: The dual fluorescence labeling of ex vivo immunoglobulin light chain amyloid fibrils stained with CR and ThT is shown. Panel (A) shows scattering patterns of the amyloid fibrils; panel (B) quantifies the amount of ThT fluorescence without CR; panel (C) quantifies the amount of CR fluorescence in the presence of ThT; and panel (D) shows the fluorescence of both CR and ThT and the quenching effect of CR on ThT.
Figure 3B:
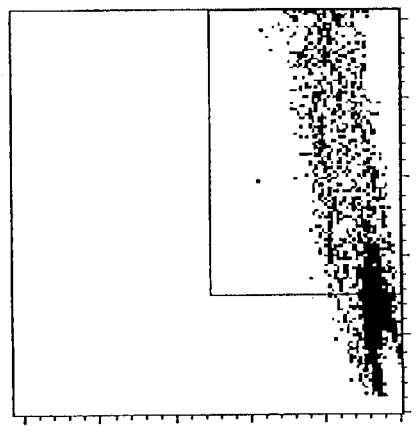
Figure 3C:
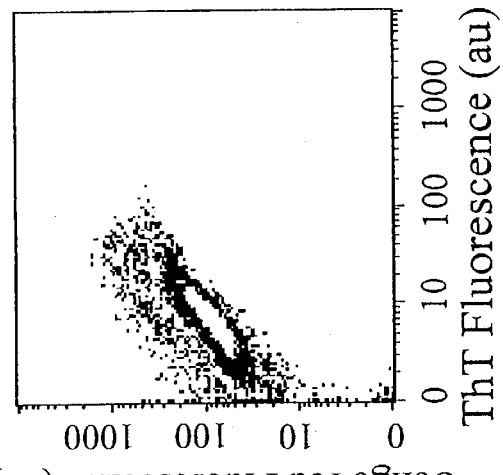
Figure 3D:
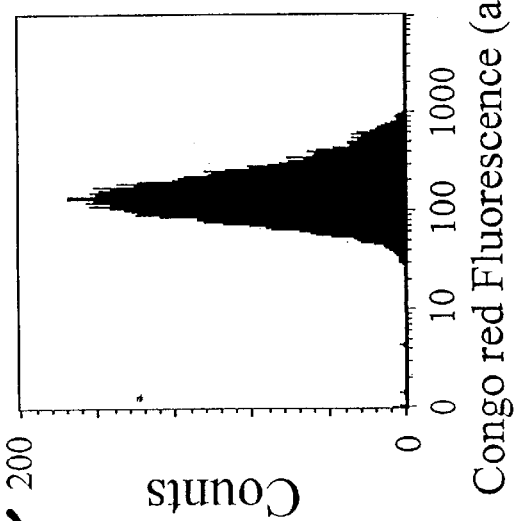
Figure 6B:
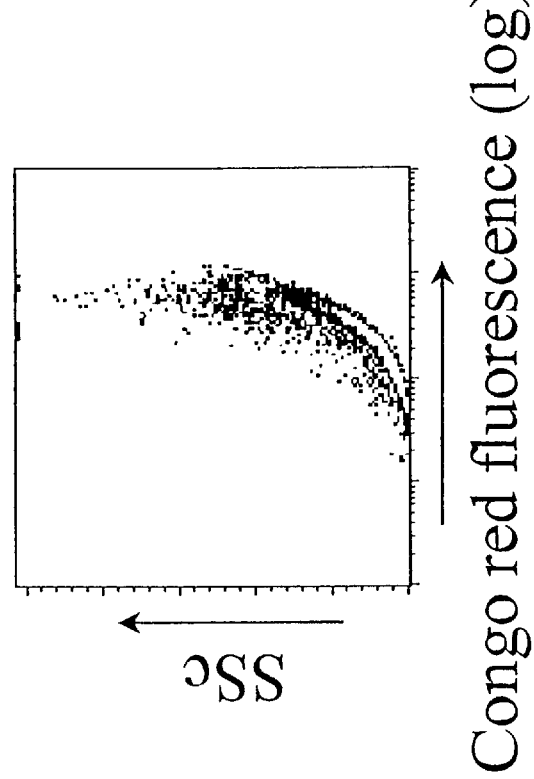
FIGS. 6A–6B: The relationship between SSC and either (A) ThT fluorescence (log mode) or (B) CR fluorescence (log mode) for synthetic Aβ (25–35) amyloid fibrils is shown.
Figure 6A:
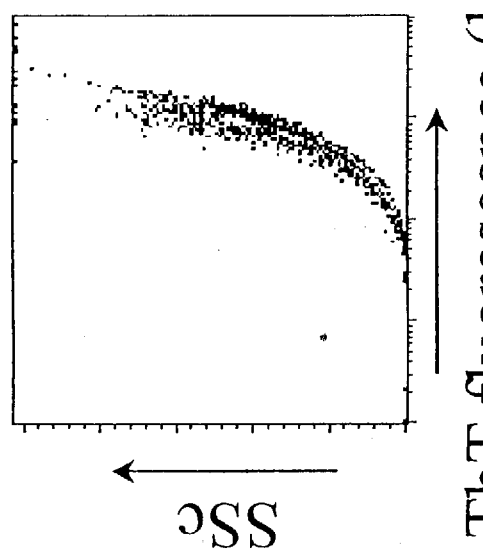

The present invention provides methods for specifically detecting the presence of amyloid fibrils in biological samples obtained from a subject using flow cytometry. The subjects contemplated for such analysis are vertebrates. More preferred subjects include primates, sheep, cows, pigs, mink, and other livestock. The most preferred subject is a human or other primate.

Biological samples, especially blood cells, have been analyzed using flow cytometry. Flow cytometry has also been utilized for the optical characterization of biological particles, as described in N. B. Purvis Jr., et al., 1996 U.S. Pat. No. 5,540,494. Other clinical methods of employing flow cytometry are known in the art. For more background on these clinical methods, see FLOW CYTOMETRY: A PRACTICAL APPROACH (M. G. Ormerod, ed., Oxford University Press, 1997); HANDBOOK OF FLOW CYTOMETRY METHODS, J. P. Robinson ed. (John Wiley & Sons 1993); BIOMEDICAL SCIENCES: CURRENT PROTOCOLS IN CYTOMETRY, J. P. Robinson ed. (John Wiley & Sons 1997); and FLOW CYTOMETRY PROTOCOLS: METHODS IN MOLECULAR BIOLOGY, M. J. Jaroszeski et al; editors (Humana Press 1997).

Detection of amyloid fibrils is used to diagnose amyloid-mediated diseases both of agent-induced origin (e.g., viral encephalopathies) and those amyloid-mediated diseases arising from genetic origins. The following diseases are some examples of amyloid-mediated diseases that may be identified: Creutzfeld-Jakob Disease (CJD), Alzheimer's disease, Kuru, transmissible cerebral amyloidoses (also known as transmissible virus dementias), familial CJD, scrapie, transmissible mink encephalopathy, bovine spongiform encephalopathy (BSE), inflammation-associated amyloid type II diabetes, primary amyloidosis, feline spongiform encephalopathy, non-transmissible cerebral amyloidosis (e.g., Alzheimer's disease), and prison-mediated diseases.

The flow cytometric method of the invention is used to monitor the effectiveness or efficacy of a specific treatment in modulating the levels of amyloid fibrils. This method can be performed by treating a subject with an agent, assaying a biological sample of the subject, such as sub-cutaneous fat biopsy tissue, for the presence of amyloid fibrnls using flow cytometry, comparing this biological sample with a previous biological sample from the subject prior to said treatment, and determining the effect of said agent on levels of amyloid fibril concentration in the subject.

The methods of the invention are also used to track the progression or regression of an amyloid fibril-mediated disease by repeatedly using flow cytometry.to detect concentrations of amyloid fibrils in biological samples and tracking the results over time.

Specific Embodiments

The detection of the presence of amyloid fibrils in a biological sample is based on the turbidity of the sample. The chemical structure of the amyloid fibril allows it to be detected using flow cytometry. This is discussed in more detail below:

Turbidity is proportional to the length of the fibril when:

The diameter is small relative to the excitation wavelength and the fibril length, and the fibril is composed of optically isotropic monomers Fibrils are randomly oriented and are monodispersed A turbidity parameter ($\tau$) can be defined exactly analogou to the extinction coefficient (Campbell & Dwek, 1984):

$I_t = I_0 \exp(-\tau ct)$ and, $\tau$ is related to 90° scattering (SSc) by, $$\tau = (16\pi R_{90})/3,$$

where $R_{90}$ is the Rayleigh ratio when $\theta = 90°$

Using these parameters, the presence of amyloid fibril formation in clinical samples can be detected using flow cytometric analyses. It is preferable, but not essential, that samples containing amyloid fibrils are subjected to flow cytometry analysis prior to staining them with a fluorescent dye in order to determine the autofluorescence of the sample. After at least one amyloidophilic dye is added to the sample, the sample is again subjected to flow cytometry analysis. This process of dyeing and analyzing is then preferably repeated with at least one additional amyloidophilic dye.

Data is collected from the flow cytometry analyses, preferably including side scatter, forward scatter, and fluorescence at each step of analysis. A means for making the appropriate calculations, such as computer software or a microprocessor, is then employed to determine whether there are amnyloid fibrils in the sample and, if so, how much. Generally, when amyloid fibrils are present in a sample, the sample shows a linear dependence between forward scatter and side scatter and the sample is positive for fluorescence with appropriate amyloidophilic dyes. A linear relationship between forward scatter and side scatter is alone inadequate for detecting the presence of amyloid fibrils, however, because a suspension of E. coli, for example, may yield similar results. Thus, specifically detecting the presence of amyloid fibrils requires fluorescence data.

One important calculation which may be made from the flow cytometry data collected from a sample is the amyloid burden index (ABI). The "burden" is the amount of amyloid present in the body fluid or tissue tested. This index aids in assessing the efficacy of treatments as well as providing staging system criteria that can be used to determine the most effective treatment to be applied.

The ABI is the average of the percentage of counts that are positive for each particular amyloidophilic dye. Thus, for example, a sample that has 50% positive counts for dye A and 60% positive counts for dye B would have an ABI equal to 55%. To determine which counts are positive and which are negative, a gate must be established, using positive and negative controls, for each wavelength used to measure fluorescence. A skilled artisan would be able to select an appropriate wavelength for a band pass filter for a z selected amyloidophilic dye. It has been found, for example, that band pass filters of 530 nm and >650 nm are effective for the detection of fluorescence of thioflavin T and Congo red, respectively.

Using a negative control, a gate is positioned on a histogram of fluorescence versus counts such that the vast majority of particles are, typically, to the left of the gate. All particles with higher fluorescence intensity than the cut-off gate are deemed positive. The positive control is then analyzed to validate the positioning of the gate. Specifically, the vast majority of the particles of the positive control should be to the right of the determined cut-off value. Preferably, correct demarcation of the gate is then confirmed using another negative control.

One of ordinary skill in the art would be able to determine a suitable gate position so as to maximize the sensitivity and selectivity—that is, minimize the amount of false positive and false negative errors—of the assay. Setting the gate to contain >97% of the particles to the left for the negative control(s) and >97% of the particles to the right for the positive control(s) has been found to be optimal for some applications.

Upon establishing the position of the gate, experimental samples are analyzed in the same way as the controls. The data should be examined to provide an absolute value of the number of positive particles in each sample so that this value can be expressed as a percentage of the total number of particles interrogated. Table II shows the ABI values for five patient samples and a positive control.

In order to maintain consistency with clinical diagnostic techniques, a somewhat arbitrary cut-off value for the ABI may be required. The ABI cut-off value may be used to reconcile differences between the flow-cytometric results and those from other clinical procedures. An ABI>12, for example, may be regarded as indicative of the presence of amyloid fibrils.

At least one positive control and at least one negative control, preferably two negative controls, should be used when determining ABI. A first negative control is an amyloid-free sample otherwise similar to the test sample. If the test sample is an abdominal fat sample, for example, then an amyloid-free abdominal fat sample of equal wet weight prepared in parallel with the test sample is preferred. Another desirable negative control is a preparation of non-fibrillar aggregates. Typical non-fibrillar aggregate samples include, for example, a 1 mg/ml suspension of a heat-denatured Bence Jones protein or a heat-denatured IgLC $V_L$. The preferred positive control is a preparation of synthetic IgLC $V_L$ amyloid fibrils that are confirmed as fibrillar by spectroscopic, microscopic and/or cytometric analyses. See Wall et al., "In vitro Immunoglobulin light chain Fibrillogenesis", Methods in Enzymology, Vol. 309 (In Press); Wall et al., "Thermodynamic Instability of Human Lambda-6 Light Chains: Correlation with Fibrillogenicity," AMYLOID (submitted).

Mixtures of amorphous and fibrillar material in suspension can be examined to determine the percent of amyloid fibril particles. The population of particles meeting the amyloid fibril criteria is expressed as a percentage of total particles analyzed. Mixed samples appear bimodal when viewed as fluorescence histograms. Amyloid fibrins exhibiting amyloidophilic dye positivity appear as one mode, and amorphous material, which is negative for the amyloidophilic dye(s), appears as another mode.

Synthetic and biological (ex vivo) samples of amyloid fibrils can be stained and analyzed using amyloidophilic dyes. Amyloidophilic dyes are those dyes that bind to amyloid fibrils. Suitable dyes include crystal violet, methyl violet, eosin, brilliant cresol violet and direct red. Preferred dyes are thioflavins, particularly thioflavin T, and Congo red.

If more than one dye is added to a sample, the order of addition may be important. It has been found, for example, that thioflavin T should be used before Congo red because the addition of Congo red before thioflavin T results in quenching of the thioflavin T fluorescence.

Another embodiment of the invention is a kit for detecting the presence of amyloid fibrils in a biological sample. The kit includes at least one positive control sample and at least one negative control sample for use in detecting amnyloid fibrils in a biological sample. The kit may also include an amyloid fibril extraction solvent; a means for calculating an Amyloid Burden Index for a biological sample, such as computer software; and amyloidophilic dyes, such as Congo red and thioflaviri T.

Both synthetic and physiological amyloid samples display a linear relationship between side scatter and forward scatter, which is believed to be indicative of the structure of the amyloid fibrils, i.e., linear aggregates composed of identical, repeating sub-units. Labeling the preparations with Congo red and/or thioflavin T results in a large fluorescent signal using propidium iodide and fluoresce in isothiocyanate filters, respectively.

While not intending to be bound by any particular theory, it is believed that the amount of thioflavin T fluorescence is proportional to the amount of dye bound to an individual amyloid fibril, which in turn is positively correlated with its length. It is anticipated that this technique will provide invaluable information regarding the evolution of amyloid fibrils from their monomeric precursors.

Using the methods described herein, it is possible to detect small amounts of amyloid fibrils in body fluids such as serum/plasma, urine and cerebrospinal fluid as well as biopsy material. The ability to screen bodily fluids as a means for diagnosing arnyloid fibrils may remove the need for invasive biopsy procedures. Also, in the case of the cerebral amyloidoses, where biopsies cannot be performed (Alzheimer's, CJD, BSE and Scrapie), these methods may provide the opportunity for diagnosing the disease prior to the onset of observable symptoms.

In addition, because the ABI is quantitative and related to the weight of biopsy material, serial analyses from a single patient can provide information on the amount and rate of deposition, which may relate to overall disease progression. Traditionally, the clinical diagnosis of amyloidoses is achieved by histologic examination of suspect tissues using alkaline-Congo red staining. Positive diagnoses are usually confirmed by electron microscopy. Although these known techniques are satisfactory for discerning positive or negative samples, neither technique is capable of yielding a quantitative measure of amyloid burden. This information is clinically important in determining the progression of a disease, as well as in providing information on the efficacy of treatment in reducing tissue amyloid content. Furthermore, ABI results can be used in the in vivo testing of anti-amyloid therapeutics.

The methods described herein have important applications in the agricultural industry as a means of testing livestock for the presence BSE ("mad cow disease") and scrapie (found in sheep and presumed to be the source of BSE in cows). Recent reports have demonstrated that sheep (inflammation-associated encephalopathy), goats (inflammation-associated encephalopathy) and chickens (spongiform encephalopathy) can develop amyloid-associated diseases.

In accordance with the present invention, as described above or as discussed in the Examples below, conventional molecular biology, microbiology, flow cytometry and recombinant DNA techniques may be employed. Such techniques are explained fully in the literature. See, for example, Sambrook, Fritsch and Maniatis, *MOLECULAR CLONING: A LABORATORY MANUAL* (Second Ed., Cold Spring Harbor Press, Cold Spring Harbor N.Y., 1989); *DNA CLONING: A PRACTICAL APPROACH*, vols. 1 and 2 (D. N. Glover ed., 1985); *OLIGONUCLEOTIDE SYNTHESIS* (M. J. Gait ed., 1984); *NUCLEIC ACID HYBRIDIZATION* (B. D. Hames and S. J. Higgins eds., 1985); *TRANSCRIPTION AND TRANSLATION* (B. D. Hames and S. J. Higgins, eds, 1984); E. Harlow and D. Lane, *ANTIBODIES: A LABORATORY MANUAL* (Cold Spring Harbor Press, Cold Spring Harbor N.Y., 1988); and Ausubel et. al., *CURRENT PROTOCOLS IN MOLECULAR BIOLOGY* (Greene Publishing Co. N.Y., 1995); *FLOW CYTOMETRY: A PRACTICAL APPROACH* (M. G. Ormerod, ed., Oxford University Press, 1997); *HANDBOOK OF FLOW CYTOMETRY METHODS*, J. P. Robinson ed. (John Wiley & Sons 1993); *BIOMEDICAL SCIENCES: CURNT PROTOCOLS IN CYTOMETRY*, J. P. Robinson ed. (John Wiley & Sons 1997); and *FLOW CYTOMETRY PROTOCOLS: METHODS IN MOLECULAR BIOLOGY*, M. J. Jaroszeski et al., editors (Humana Press 1997).

The following working examples, which disclose the use of flow cytometry to detect amyloid fibrils in biological samples such as blood, specifically point out preferred embodiments of the present invention. These examples are not to be construed as limiting in any way the scope of the invention. Other examples involving flow cytometry and the detection of amyloid fibrils for therapeutic, diagnostic, research, and agricultural purposes will be apparent to one skilled in the art.

EXAMPLE 1

Isolation of Amyloid Fibrils from Tissue and Fat Aspirate

Fat tissue was obtained by fine-needle aspirate of biopsy tissue from patients diagnosed with AL amyloidosis. The tissue was suspended in 500 μl of sterile filtered phosphate buffered saline (PBS, 150 mM NaCl, 5 mM $NaH_2PO_4$, and 5 mM $Na_2HPO_4$) and sonicated on ice for two periods of 45 seconds separated by 2 minutes on ice. Disruption of the tissue was performed using a sonication probe (Maker) emitting 2 Watts. The samples were then centrifuged at 17,000×g for 30 minutes at room temperature, resulting in a layer of lipid suspended at the air-water interface and a pellet containing amyloid fibrils. The pellet was isolated and washed by centrifugation as above, and finally resuspended in 500 μl of PBS. The lipid-free supernatant was also collected for cytometric analysis.

Three samples of human AL-amyloid extract were prepared from various organs by the standard, water-extraction method described by Pras et al., "The Characterization of Soluble Amyloid Prepared in Water," *JOURNAL OF CLINICAL INVESTIGATION* (1962) 47, 924–33. The first HIG is composed of a κ I light chain, the second TYL a λ IIIa $V_L$ light chain, and the third JTO, a λ VI light chain. The resultant amyloid was either stored as an aqueous emulsion at 4 mg/ml (total protein), or lyophilized to dryness, both preparations were stored at 4° C. Solutions for analysis were prepared at 1 mg/ml total protein in PBS. Duplicate samples were subjected to mild sonication immediately prior to examination.

AA amyloid was obtained from the liver of an 8-month-old mouse transgenic for the human IL-6 gene, as described by Solomon et al., "Transgenic Mouse Model of AA Amyloidosis," *AMERICAN JOURNAL OF PATHOLOGY* (1999) 154 (4), 1267–72. The liver and spleen of the mouse had been shown to contain plentiful amyloid deposits based upon the characteristic blue-green birefringence of Congo red stained samples under polarizing light microscopy. Amyloid extract was prepared in the same way as that described above for fat tissue.

In Vitro Preparation of Amyloid Fibrils

Amyloid fibrils were prepared from the following proteins and peptides. Aβ (25–35) amyloid fibrils were formed by the addition of PBS to the peptide to a final concentration of 1 mg/ml; under these conditions fibrillogenesis is spontaneous.

Recombinant immunoglobulin light-chain $V_L$ proteins, $recV_L$WIL and $recV_L$JTO are described by Wall et al, "In vitro Immunoglobulin light chain Fibrillogenesis," *METHODS IN ENZYMOLOGY*, Vol. 309 (In Press). See also Wall et al., "Thermodynamic Instability of Human Lambda-6 Light Chains: Correlation with Fibrillogenicity", AMYLOID (submitted). Briefly, the following protocol was used. A 1 mg/ml solution of protein/peptide (used interchangeably hereafter) is prepared in phosphate-buffered saline (PBS) using HPLC-grade water and adjusted to pH 7.5. The solution is passed through a 0.2 mm pore-sized filter to remove preformed aggregates. Fibrillogenesis is initiated by mixing the protein solution at 37° C for up to 5 days (higher temperatures my be used if an increased reaction speed is required). Mixing may be performed in a glass test tube, plastic cuvette or microplate. For production of bulk quantities a 1 ml volume of protein solution is placed in a 10 ml-volume glass test tube and placed in a thermostatted orbital shaker (Queue Orbital Shaker). The protein solution is agitated at 37° C. and 225 revolutions per minute. Solution turbidity arising from amyloid fibril formation can be detected within 5 days when VL fragments are used.

The proteins were subjected to gentle mixing at 0.07 mg/ml in a fluorimetric cuvette containing 6 μM thioflavin T, at 40° C.; under these conditions fibrillogenesis occurs within 1 hour.

The amyloid fibrils of both Aβ (25–35) and $V_L$ origin were shown to exhibit the characteristic tinctorial properties of amyloid fibrils when stained with Congo red. They showed an increase in the fluorescence of thioflavin T when excited at 450 nm. And they showed unbranching, linear fibril morphology when negatively stained and examined by electron microscopy. Certain amyloid fibril sarnples were subjected to mild sonication post-formation, immediately prior to flow-cytometric analysis, in order to disaggregate large particles.

Biological samples of cerebrospinal fluid, plasma, serum and urine are prepared by concentrating them followed by centrifugation in order to increase the concentration of amyloid particles in the sample.

In Vitro Preparation of Non-Fibrillar Protein Aggregates

Aggregates were formed using the following isolated Bence Jones proteins: HIG (κI), BEF (κI), CRO (κI), CAG, and DRU. The following two methods were employed: (1) mixing a 0.05 mg/ml solution at room temperature, in a fluorimetric cuvette for 5 hours, or (2) by extensive sonication of a 1 mg/ml solution for approximately 500 seconds, with intermittent cooling periods to prevent the solution from overheating. Non-fibrillar aggregates are characterized by: (1) a lack of blue-green birefringence when stained with Congo red and observed under polarized light; (2) no increase in the fluorescence intensity of thioflavin T when excited at 450 nm; and (3) an amorphous appearance when negatively stained with 2% uranyl acetate and visualized by electron microscopy.

Flow-Cytometric Analysis of Synthetic and Extracted Amyloid Fibrils

Ex vivo (physiological) and synthetic amyloid fibrils were suspended in PBS at approximately 1 mg/ml. The solutions were passed through a filter with a 6 μm pore-size to remove large aggregates. To this was added 10 μl of 1 mM thioflavin T solution or 0.01% Congo red and the solution was mixed for 2 minutes by manual agitation. Both dyes may be added to the same sample as follows: thioflavin T is added first and the sample is analyzed using collection data on forward scatter, side scatter and fluorescence (using FITC filters) in both linear and logarithmic modes. Congo red was then added to the sample and data collected in the same way using the propidium iodide or rhodamine filter pairs to detect Congo red fluorescence.

Data was collected using a Macintosh-integrated, Becton Dickinson Flow Cytometer, with CellQuest software. Gain settings used for the analysis of synthetic amyloid fibrils are shown in Table I. For comparison, the optimum settings for routine immunophenotyping are also presented. The major difference in instrument settings is the value of the forward angle light-scatter detector voltage, which is an order of magnitude greater than that used for cells, indicating the low forward scatter signal of amyloid fibrils. All other values are comparable.

TABLE I

| GAIN OPTION | FSC (Lin) | SSC (Lin) | FL1 (Log) | FL2 (Log) | FL3 (Log) |
|---|---|---|---|---|---|
| SETTINGS FOR AMYLOID FIBRIL DETECTION | | | | | |
| Amplifier Gain | 6.64 | 1.00 | 1.00 | 1.00 | 1.00 |
| Detector (V) | 10 | 308 | 674 | 476 | 524 |
| SETTINGS FOR IMMUNOPHENOTYPING | | | | | |
| Amplifier Gain | 2.31 | 1.00 | 1.00 | 1.27 | 1.00 |
| Detector (V) | 1 | 333 | 664 | 473 | 550 |

FL1, FL2 and FL3 refer to fluorescence signals from three photomultipliers corresponding to 530 nm, 585 nm and >650 nm band pass filters, respectively.

Data was analyzed for the presence of thioflavin T and/or Congo red fluorescence, with respect to suitable negative control samples. Amyloid particles were characterized by a distinct pattern of fluorescence with respect to side scatter, as well as by an increase in fluorescence signal with respect to the negative control samples.

EXAMPLE 2

Quantification of Amyloid Burden as Determined from Patient Fat Biopsies

Figure 7A:
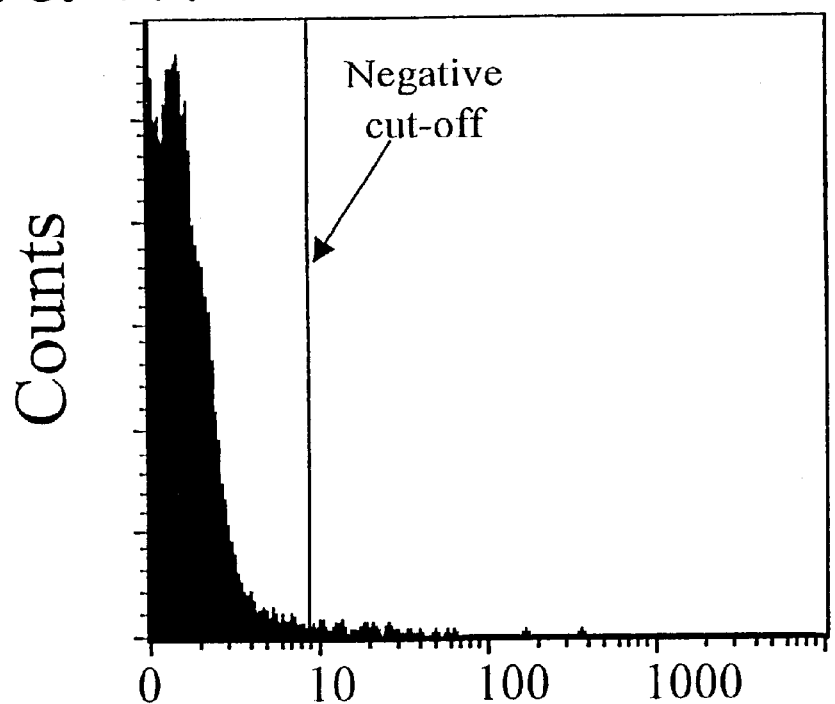
FIGS. 7A–7B: The positioning of a cut-off gate for determining the ABI of a sample is shown. Panel (A) shows the position of the gate as determined using a negative control sample, i.e., a preparation of non-fibrillar aggregates prepared by heat denaturation. The protein sample is in PBS at 0.1 mg/ml and 0.001% aqueous Congo red. A similar result is obtained using an amyloid-free, abdominal fat sample. Panel (B) shows the positioning of the gate using a positive control sample, i.e., a preparation of synthetic IgLC $V_L$ amyloid fibrils in PBS at 50 ug/ml.
Figure 7B:
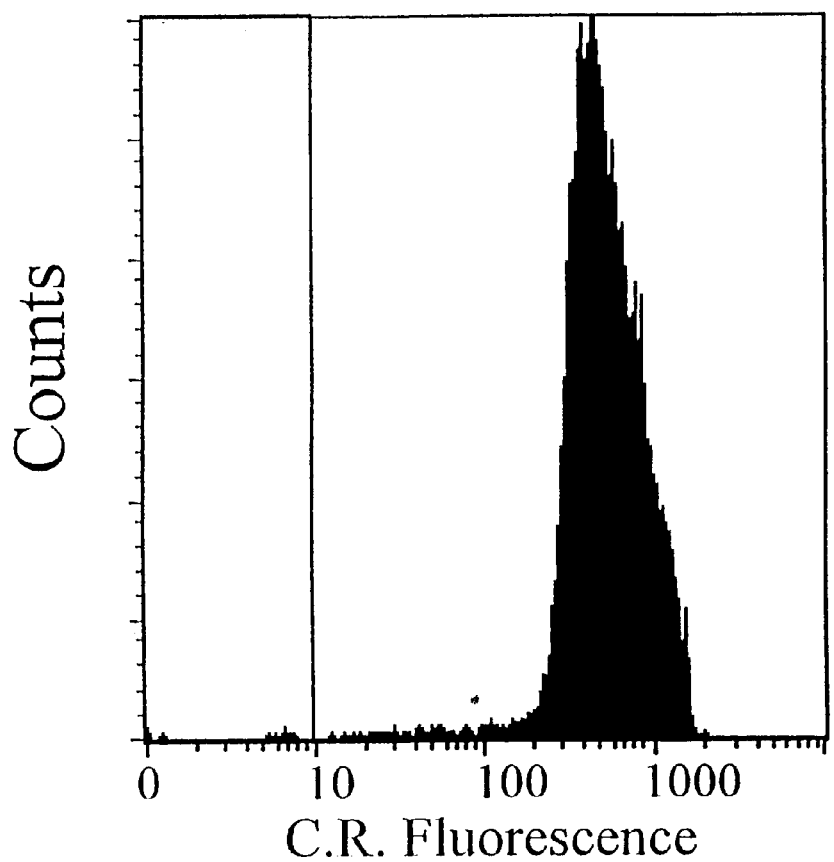

Fat samples both from patients known to have high amyloid concentrations and from human controls were obtained using needle aspirations as described in Example 1. Control samples were used to determine the optimum placement of the gates distinguishing positive and negative particles. FIG. 7, for example, demonstrates the position of a cut-off gate for determining the ABI of a sample.

Table II compares the detection of the presence of amyloid fibrils in a sample using the flow cytometric method of the invention to the clinical results obtained from a Congo red birefringence assay using polarized light microscopy. The Congo red birefringence assay using polarized light microscopy is described, for example, in R. A. Kyle, "Plasma Cell Disorders," in *CECIL TEXTBOOK ON MEDICINE*, 958–68. As can be seen from the Table II, patients with advanced disease had consistently higher ABI values than did those patients with early stage disease.

TABLE II

| Patient | CR Assay (Staging Value) | Mean Gated Points | % Points in ThT+ gate (X) | % Points in CR+ gate (Y) | ABI {(X + Y)/2} |
|---|---|---|---|---|---|
| Mal | III/IV | 10,868 | 14.2 | 99.5 | 56.85 |
| McN | III/IV | 9,583 | 4.6 | 35.6 | 22.20 |
| Bro | III | 10,430 | 6.0 | 38.4 | 20.12 |
| Hea | II | 9,453 | 1.7 | 24.5 | 13.10 |
| Leh | 0 | 10,196 | 1.3 | 17.6 | 9.45 |
| Positive Control | n.a | 8,191 | 98.8 | 99.5 | 99.15 |

CR, Congo Red; ThT, thioflavin T; n.a., not applicable because the positive control was made up of amyloid fibrils prepared in vitro; FC, flow cytometry One of ordinary skill in the art would appreciate the precautions and improvements that can be taken to maximize the effectiveness of the assay. DNAase, for example, can be used to remove contaminating DNA fragments which bind Congo red and thioflavin T and which may result in false positives. Further, flow cytometry with a tunable laser can be used to enhance the sensitivity of the fluorescence detection. The side scatter measurements can be calibrated using "rods" of defined length so as to allow quantitative determination of amyloid fibril lengths.

All references, articles, texts and patents referred to above are hereby incorporated by reference in their entirety.

What is claimed is:

1. A kit for detecting the presence of amyloid fibrils in a biological sample comprising a means for determining an amyloid burden index (ABI) for the biological sample and at least one control sample.

2. The kit of claim 1, Wherein the control sample contains amyloid fibrils.

3. The kit of claim 2, wherein the amyloid fibrils are synthetic fibrils.

4. The kit of claim 3, wherein the synthetic fibrils are IgLCV$_L$ amyloid fibrnls.

5. The kit of claim 1, wherein the control sample is free of amyloids.

6. The kit of claim 5, wherein the control sample is an amyloid-free abdominal fat sample.

7. The kit of claim 1, wherein the control sample is a non-fibrillar aggregate sample.

8. The kit of claim 7, wherein the non-fibrillar aggregate sample is heat-denatured Bence Jones protein sample or a heat-denatured IgLCV$_L$ amyloid fibril sample.

9. The kit of claim 1, wherein the kit further comprises an amyloid fibril extraction solvent.

10. The kit of claim 1, wherein the kit further comprises an amyloidophilic dye.

11. The kit of claim 10, wherein the amyloidophilic dye is thioflavin T or Congo red.

12. The kit of claim 1, wherein the kit further comprises a means for collecting the biological sample.

13. A kit for monitoring the effectiveness of an agent in treating a disease mediated by abnormal amyloid fibril concentrations in a subject comprising a means of determining the amyloid burden index (ABI) of a biological sample taken from the subject, and a control sample.

14. The kit of claim 13, wherein the control sample contains amyloid fibrils.

15. The kit of claim 14, wherein the amyloid fibrils are synthetic fibrils.

16. The kit of claim 15, wherein the synthetic fibrils are IgLCV$_L$ amyloid fibrils.

17. The kit of claim 13, wherein the control sample is free of amyloids.

18. The kit of claim 17, wherein the control sample is an amyloid-free abdominal fat sample.

19. The kit of claim 13, wherein the control sample is a non-fibrillar aggregate sample.

20. The kit of claim 19, wherein the non-fibrillar aggregate sample is heat-denatured Bence Jones protein sample or a heat-denatured IgLCV$_L$ amyloid fibril sample.

21. The kit of claim 13, wherein the kit further comprises an amyloid fibril extraction solvent.

22. The kit of claim 13, wherein the kit further comprises an amyloidophilic dye.

23. The kit of claim 22, wherein the amyloidophilic dye is thioflavin T or Congo red.

24. The kit of claim 13, wherein the kit further comprises the agent for treating a disease.

25. The kit of claim 13, wherein the kit further comprises a means for collecting a biological sample from the subject.

* * * * *